United States Patent
Harada et al.

(10) Patent No.: US 9,131,897 B2
(45) Date of Patent: Sep. 15, 2015

(54) CATHETER FOR MEASURING ELECTRIC POTENTIAL

(75) Inventors: Hiroyuki Harada, Otsu (JP); Motoki Takaoka, Otsu (JP)

(73) Assignee: Toray Industries, Inc. (JP)

( * ) Notice: Subject to any disclaimer, the term of this patent is extended or adjusted under 35 U.S.C. 154(b) by 384 days.

(21) Appl. No.: 13/701,879

(22) PCT Filed: Jun. 6, 2011

(86) PCT No.: PCT/JP2011/062889
§ 371 (c)(1),
(2), (4) Date: Dec. 4, 2012

(87) PCT Pub. No.: WO2011/155424
PCT Pub. Date: Dec. 15, 2011

(65) Prior Publication Data
US 2013/0079614 A1    Mar. 28, 2013

(30) Foreign Application Priority Data
Jun. 8, 2010  (JP) ................ 2010-130774

(51) Int. Cl.
*A61B 5/042*  (2006.01)
*A61B 18/14*  (2006.01)
*A61B 5/00*   (2006.01)
*A61B 17/00*  (2006.01)
*A61B 18/00*  (2006.01)

(52) U.S. Cl.
CPC .............. *A61B 5/6852* (2013.01); *A61B 5/042* (2013.01); *A61B 5/0422* (2013.01); *A61B 18/1492* (2013.01); *A61B 2017/00039* (2013.01); *A61B 2017/00243* (2013.01); *A61B 2018/0022* (2013.01); *A61B 2018/00357* (2013.01); *A61B 2018/00577* (2013.01)

(58) Field of Classification Search
CPC .... A61B 5/042; A61B 5/0422; A61B 5/6852; A61B 18/1492
USPC .............................. 600/374; 606/41
See application file for complete search history.

(56) References Cited

U.S. PATENT DOCUMENTS

| 7,269,453 B2 * | 9/2007 | Mogul ............ 600/374 |
| 2002/0029062 A1 | 3/2002 | Satake |
| 2004/0019349 A1 | 1/2004 | Fuimaono et al. |
| 2007/0066878 A1 | 3/2007 | Worley et al. |

FOREIGN PATENT DOCUMENTS

| JP | 9-140803 A | 6/1997 |
| JP | 2002-078809 A | 3/2002 |
| JP | 2008-508064 A | 3/2008 |
| JP | 4062935 B2 | 3/2008 |
| JP | 2009-508589 | 3/2009 |
| JP | 4417052 B2 | 2/2010 |
| JP | 2010-268847 A | 12/2010 |
| WO | 2007/091348 A1 | 8/2007 |

* cited by examiner

*Primary Examiner* — Lee S Cohen
(74) *Attorney, Agent, or Firm* — DLA Piper LLP (US)

(57) ABSTRACT

A highly safe catheter that measures electric potential can be inserted into a cardiac chamber together with a balloon-tip ablation catheter and is able to prevent abnormal heat generation at electric potential-measuring electrodes even when high-frequency current is distributed. The catheter includes a shaft having electric potential-measuring electrodes, a metal portion with a length of 2 mm or more, and a lumen passing therethrough from a proximal end to a distal end in the longitudinal direction; and a metal wire inserted through the lumen and connected to the metal portion.

6 Claims, 2 Drawing Sheets

CATHETER FOR MEASURING ELECTRIC POTENTIAL

RELATED APPLICATIONS

This is a §371 of International Application No. PCT/JP2011/062889, with an international filing date of Jun. 6, 2011 (WO 2011/155424 A1, published Dec. 15, 2011), which is based on Japanese Patent Application No. 2010-130774, filed Jun. 8, 2010, the subject matter of which is incorporated herein by reference.

TECHNICAL FIELD

This disclosure relates to a catheter for measuring electric potential.

BACKGROUND

Catheter ablation is a method of treating arrhythmia by inserting an ablation catheter into a cardiac chamber and cauterizing cardiac muscle tissue with electrodes attached to the distal end of the catheter. In that method, it is common to perform an electrophysiological examination using a catheter for measuring electric potential to determine the cautery site and confirm therapeutic effects. Catheters for measuring electric potential are constituted to comprise a plurality of electric potential-measuring electrodes, electric potential-measuring electrode leads connected to the electric potential-measuring electrodes, and an electric potential-measuring apparatus connector. A measurement of electric potential of cardiac muscle tissue allows for confirmation of the cauterized site and the cautery site.

In recent years, a balloon-tip ablation catheter in which a balloon attached at the distal side of a catheter is introduced percutaneously into inferior vena cava to reach the right atrium of the heart and the left atrium through the atrial septum and cardiac muscle tissue is cauterized by heating the balloon inflated therewith a high-frequency current has been developed (JP 2002-78809 A and Japanese Patent No. 4062935) and become the mainstream of catheter ablation. Even in the treatment using a balloon-tip ablation catheter, an electrophysiological examination using a catheter for measuring electric potential is still required to determine the cautery site and confirmation of therapeutic effects, and thus a balloon-tip ablation catheter also having an electrophysiological examination function has also been reported (Japanese Patent No. 4417052).

However, the previously-reported conventional balloon-tip ablation catheters also having an electrophysiological examination function proved to be at high risk of causing, for example, thrombosis, excessive cauterization, and tissue perforation in an affected area because, when a balloon is heated by distributing high-frequency current between a return electrode outside the patient's body and a high-frequency current distributing electrode in the balloon, the high-frequency current is distributed also between the return electrode and electric potential-measuring electrodes, causing a phenomenon of abnormal heat generation at the electric potential-measuring electrodes.

On the other hand, when treatment is carried out with a catheter for measuring electric potential being provided separately from a balloon-tip ablation catheter to ensure patient safety, it is necessary to once evulse the balloon-tip ablation catheter from a patient and then again insert the catheter for measuring electric potential into a cardiac chamber to perform an electrophysiological examination, and a prolonged procedure time and the associated increased burden on physicians and patients are unavoidable.

Thus, it could be helpful to provide a highly safe catheter for measuring electric potential that can be inserted into a cardiac chamber together with a balloon-tip ablation catheter and is able to prevent abnormal heat generation at electric potential-measuring electrodes even when high-frequency current is distributed.

SUMMARY

We thus provide (1) to (8) below:
(1) A catheter for measuring electric potential, comprising: a shaft having electric potential-measuring electrodes, a metal portion with a length of 2 mm or more, and a lumen passing therethrough from a proximal end to a distal end in the longitudinal direction; and a metal wire inserted through the lumen and connected to the metal portion.
(2) The catheter for measuring electric potential according to (1) above, wherein the above-described electric potential-measuring electrodes are attached at a distal side in the longitudinal direction of the above-described shaft, and the above-described metal portion is located distally relative to the position of the above-described electric potential-measuring electrodes in the longitudinal direction of the above-described shaft.
(3) The catheter for measuring electric potential according to (1) or (2) above, wherein the length of the above-described metal portion is 2 to 50 mm.
(4) The catheter for measuring electric potential according to any one of (1) to (3) above, wherein the above-described metal wire is electrically insulated.
(5) A catheter for measuring electric potential, comprising a metallic shaft having electric potential-measuring electrodes and a lumen extending in the longitudinal direction.
(6) The catheter for measuring electric potential according to (5) above, wherein the above-described metallic shaft is obtained by forming a metal wire into a coil shape.
(7) The catheter for measuring electric potential according to (5) or (6) above, wherein the above-described metallic shaft is electrically insulated.
(8) A balloon-tip ablation catheter system, comprising the catheter for measuring electric potential according to any one of (1) to (7) above and a balloon-tip ablation catheter comprising a lumen passing therethrough from a proximal end to a distal end in the longitudinal direction, wherein the above-described catheter for measuring electric potential is inserted through the lumen of the above-described balloon-tip ablation catheter.

Abnormal heat generation at electric potential-measuring electrodes of a catheter for measuring electric potential can be prevented even when high-frequency current is distributed, and excessive cauterization of cardiac muscle tissue can be prevented. Further, a catheter for measuring electric potential can be inserted into a cardiac chamber simultaneously with a balloon-tip ablation catheter, and therefore burden on physicians and patients can be significantly reduced.

DESCRIPTION OF SYMBOLS

Figure 1:
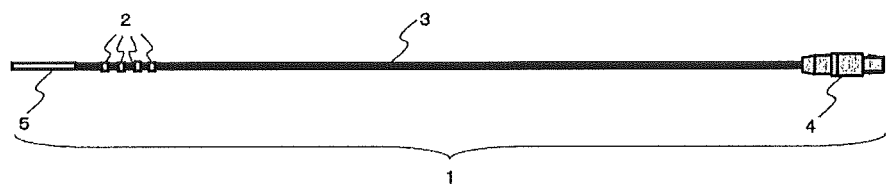
FIG. 1 is a schematic view of the catheter for measuring electric potential according to the first example.

1: Catheter for measuring electric potential
2: Electric potential-measuring electrodes
3: Shaft
4: Electric potential-measuring apparatus connector
5: Distal metal portion
6: Metal wire
7: Electric potential-measuring electrode leads
8: Balloon-tip ablation catheter
9: Balloon
10: High-frequency current distributing electrode
11: Temperature sensor
12: Outer tubular body
13: Inner tubular body
14: High-frequency power generator connector
15: High-frequency power generator
16: Luer lock
17: Y-shaped connector
18: Return electrode
19: Return electrode lead
20: T-type thermocouple
21: Temperature data logger

DETAILED DESCRIPTION

Preferred examples will now be described in detail with reference to the drawings, but the disclosure is not limited to these examples. Like numbers refer to like elements, and repetitive descriptions will be omitted. The scale of the drawings does not necessarily correspond to those in the description. It should be understood that "length" as used herein represents the length in the longitudinal direction.

The catheter for measuring electric potential is characterized by comprising: a shaft having electric potential-measuring electrodes, a metal portion with a length of 2 mm or more, and a lumen passing therethrough from a proximal end to a distal end in the longitudinal direction; and a metal wire inserted through the lumen and connected to the metal portion.

FIG. 1 is a schematic view of the catheter for measuring electric potential according to the first example.

The catheter for measuring electric potential 1 shown in FIG. 1 comprises a plurality of electric potential-measuring electrodes 2, a distal metal portion 5, a shaft 3, and an electric potential-measuring apparatus connector 4.

The number of the electric potential-measuring electrodes 2 attached to the shaft 3 is preferably 1 to 16 and more preferably 4 to 10. As a material of the electric potential-measuring electrodes 2, a highly conductive metal is preferred, and examples thereof include silver, gold, platinum, copper, and SUS. The electric potential-measuring electrodes 2 are preferably attached at the distal side in the longitudinal direction of the shaft 3, as shown in FIG. 1.

As shown in FIG. 1, when the electric potential-measuring electrodes 2 are attached to the surface of the shaft 3, the shape of the electric potential-measuring electrodes 2 is preferably cylindrical. The length of the cylinder-shaped electric potential-measuring electrodes 2 is preferably 0.5 to 2.0 mm and more preferably 1.0 to 2.0 mm.

As a material of the distal metal portion 5, i.e., "the metal portion," a highly conductive metal is preferred, and examples thereof include silver, gold, platinum, copper, and SUS. "The metal portion" is preferably attached at the distal side in the longitudinal direction of the shaft 3, more preferably located distally relative to the position of the electric potential-measuring electrodes 2 in the longitudinal direction of the shaft 3 like the distal metal portion 5 shown in FIG. 1, and still more preferably attached to the distal end of the shaft 3.

To prevent abnormal heat generation around the distal metal portion 5 and the electric potential-measuring electrodes 2, the length of the distal metal portion 5 is preferably 2 mm or more and more preferably 5 mm or more. In view of the risk, for example, of reduction in operability, cardiac wall perforation, or vascular injury, the length of the distal metal portion 5 is preferably not more than 50 mm and more preferably not more than 25 mm.

"The metal portion," the form of which is not particularly restricted, may be formed by inserting a shaft made of highly conductive metal or the like through a lumen of the shaft 3 and removing a portion of the shaft 3 to expose the highly conductive metal or the like, or may be formed by removing a portion of the coating of the shaft 3 that is made of highly conductive metal or the like coated with other materials to expose the highly conductive metal or the like. Further, a portion of the shaft made of highly conductive metal or the like that has been exposed at the distal end of the shaft 3 as a result of inserting a shaft made of highly conductive metal or the like that is longer than the shaft 3 through a lumen of the shaft 3 may be defined as the distal metal portion 5.

Because the catheter for measuring electric potential is used inserted through a lumen of a balloon-tip ablation catheter, the length of the shaft 3 is preferably longer than the whole length of the balloon-tip ablation catheter, more preferably 600 to 1800 mm, and more preferably 700 to 1300 mm. In addition, because the catheter for measuring electric potential is used inserted through a lumen of a balloon-tip ablation catheter, the outer diameter of the shaft 3 is preferably 0.6 to 1.2 mm and more preferably 0.8 to 1.2 mm.

As a material of the shaft 3, materials having low conductivity, excellent antithrombogenicity, and flexibility are preferred, and examples thereof include fluororesins, polyamide resins, polyurethane resins, and polyimide resins. For example, when the shaft 3 is made of highly conductive metal or the like coated with other materials as described above, it is preferable to use as the "other material" the fluororesins or the like described above.

The shape of the shaft 3 at the region where a plurality of the electric potential-measuring electrodes 2 are attached may be not only linear as shown in FIG. 1, but also looped or the like. In the shaft 3, the length of the region where a plurality of the electric potential-measuring electrodes 2 are attached is preferably 20 to 100 mm and more preferably 30 to 80 mm. Further, the intervals between the electric potential-measuring electrodes 2 in the case where three or more electric potential-measuring electrodes 2 are attached are preferably equal regardless of the shape of the shaft.

As shown in FIG. 1, when the distal metal portion 5 is located distally relative to the position of the electric potential-measuring electrodes 2 in the longitudinal direction of the shaft 3, the interval between the electric potential-measuring electrodes 2 attached at the most distal side and the distal metal portion 5 is preferably 5 to 50 mm and more preferably 10 to 40 mm.

Figure 2:
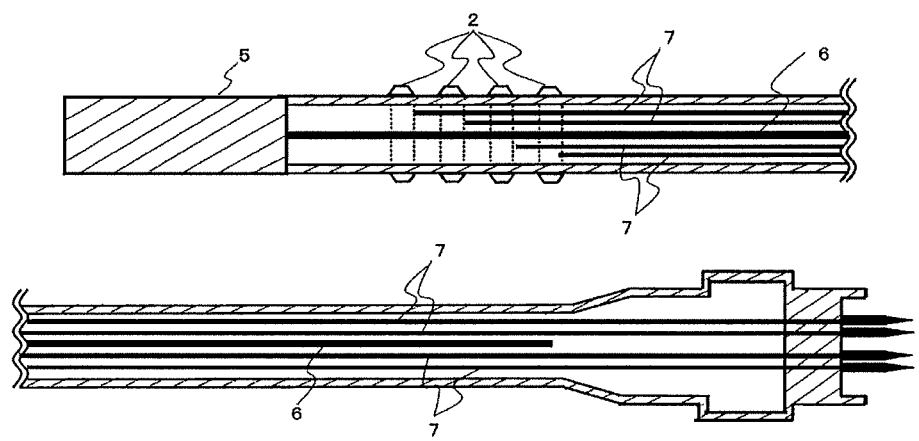
FIG. 2 is a schematic view illustrating a cross section vertical to the longitudinal direction the catheter for measuring electric potential according to the first example.

FIG. 2 is a schematic view illustrating a cross section vertical to the longitudinal direction the catheter for measuring electric potential according to the first example.

In the catheter for measuring electric potential 1 shown in FIG. 2, the shaft has a lumen passing therethrough from a proximal end to a distal end in the longitudinal direction, and a metal wire 6 and a plurality of electric potential-measuring electrode leads 7 are inserted through the lumen. The distal end of the metal wire 6 is connected to the distal metal portion 5, and the distal end of the electric potential-measuring electrode leads 7 is connected to the electric potential-measuring electrodes 2, respectively. Examples of the connection method include, but are not limited to, connections by soldering, welding, and caulking. Alternatively, the metal wire 6 and the distal metal portion 5 may be formed integrally from the same material in advance.

The diameters of the metal wire 6 and the electric potential-measuring electrode leads 7 are preferably 0.1 to 1 mm and more preferably 0.2 to 0.5 mm. Examples of the material of the metal wire 6 and the electric potential-measuring electrode leads 7 include highly conductive metals such as copper, silver, gold, platinum, tungsten, and alloy, and the electric potential-measuring electrode leads 7 is preferably coated with an electrically insulating protective covering such as a fluororesin to prevent a short circuit.

The proximal end of the electric potential-measuring electrode leads 7 is connected to the electric potential-measuring apparatus connector 4 shown in FIG. 1. Examples of the material of a sheathing of the electric potential-measuring apparatus connector 4 include low-conductive polysulfones, polycarbonates, and vinyl chloride resins. A plurality of metal pins are arranged inside the electric potential-measuring apparatus connector 4, and the electric potential-measuring electrode leads 7 are connected to the metal pins. Examples of the connection method include, but are not limited to, connections by soldering, welding, and caulking.

The proximal end of the metal wire 6 is preferably electrically insulated to inhibit the distribution of high-frequency current between a return electrode and the electric potential-measuring electrodes and prevent abnormal heat generation at the distal metal portion 5. "Electrically insulated" herein refers to a state in which the proximal end of the metal wire 6 does not have any electrical connection including grounding (earthing). Examples of the case where the proximal end of the metal wire 6 is "electrically insulated" include a state in which the proximal end of the metal wire 6 is not connected to or contacted with anything as shown in FIG. 2. If not an electrical connection, contact of the proximal end of the metal wire 6 with, for example, the electric potential-measuring apparatus connector 4 also provides the same effect.

To prevent abnormal heat generation due to concentration of high-frequency current at the metal wire 6, the length of the metal wire 6 is preferably 300 mm or more and more preferably 500 mm or more.

The catheter for measuring electric potential according to the second example is characterized by comprising a metallic shaft having electric potential-measuring electrodes and a lumen extending in the longitudinal direction.

The catheter for measuring electric potential according to the second example is able to provide the same effect as that of the catheter for measuring electric potential according to the first example having the distal metal portion 5 by using an entirely metallic shaft. Examples of the material of the metallic shaft of the catheter for measuring electric potential according to the second example include highly conductive metals such as copper, silver, gold, platinum, tungsten, and alloy. In the catheter for measuring electric potential according to the second example, to improve the accuracy of the measurement of electric potential of cardiac muscle tissue, it is preferred that a low-conductive material such as a fluororesin, a polyamide resin, a polyurethane resin, or a polyimide resin be arranged between the electric potential-measuring electrodes and the shaft, i.e., that the electric potential-measuring electrodes and the shaft be electrically insulated.

The metallic shaft of the catheter for measuring electric potential according to the second example is preferably one obtained by forming a metal wire into a coil shape to ensure pliability. The "coil shape" herein refers to a state in which a metal wire is spirally wound into a cylindrical shape. The metallic shaft of the catheter for measuring electric potential according to the second example is preferably electrically insulated.

The diameter of a metal wire that forms the metallic shaft of the catheter for measuring electric potential according to the second example is preferably 0.1 to 0.3 mm and more preferably 0.2 to 0.3 mm.

The number, material, attachment position, and the like of the electric potential-measuring electrodes of the catheter for measuring electric potential according to the second example are preferably the same as those of the catheter for measuring electric potential 1 according to the first example.

Figure 3:
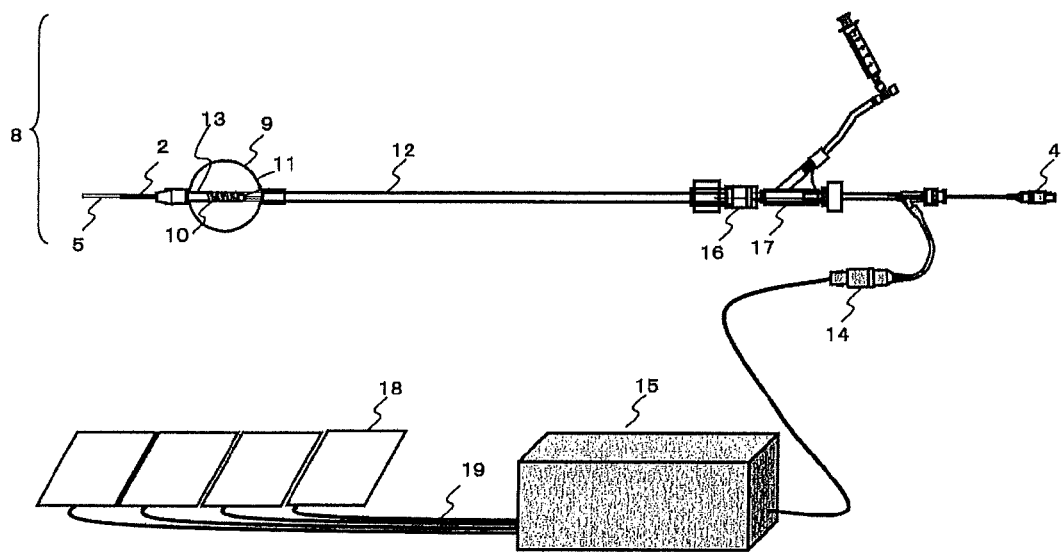
FIG. 3 is a schematic view of a balloon-tip ablation catheter system in which the catheter for measuring electric potential according to the first example is inserted through a lumen of a balloon-tip ablation catheter.

FIG. 3 is a schematic view of a balloon-tip ablation catheter system in which the catheter for measuring electric potential according to the first example is inserted through a lumen of a balloon-tip ablation catheter.

The balloon-tip ablation catheter system shown in FIG. 3 is composed broadly of the catheter for measuring electric potential according to the first example, and a balloon-tip ablation catheter 8 and a high-frequency power generator 15.

The balloon-tip ablation catheter 8 comprises at its distal side a balloon 9 that is inflatable and shrinkable, and further comprises a double cylinder type shaft, wherein an inner tubular body 13 is inserted into a lumen of an outer tubular body 12, and the inner tubular body 13 is able to slide in the longitudinal direction. The distal end of the balloon 9 is fixed near the distal end in the longitudinal direction of the inner tubular body 13, and the proximal end of the balloon 9 is fixed near the distal end in the longitudinal direction of the outer tubular body 12. A high-frequency current distributing electrode 10 and a temperature sensor 11 are arranged inside the balloon 9.

The shape of the balloon 9 may be any shape as long as it fits blood vessel, and examples of such shapes include globular shape or onion shape with a diameter of 20 to 40 mm. The film thickness of the balloon 9 is preferably 20 to 150 μm and more preferably 20 to 120 μm.

As a material of the balloon 9, stretchable materials having excellent antithrombogenicity are preferred, and polyurethane polymeric materials are more preferred. Examples of polyurethane polymeric materials include thermoplastic polyether urethane, polyether polyurethane urea, fluorine polyether urethane urea, polyether polyurethane urea resins, and polyether polyurethane urea amide.

The length of the outer tubular body 12 and the inner tubular body 13 is preferably 500 to 1700 mm and more preferably 600 to 1200 mm. For the outer diameter of the outer tubular body 12 and the inner tubular body 13, because of the use with the catheter for measuring electric potential being inserted through the lumen of the balloon-tip ablation catheter, the inner diameter of the inner tubular body 13 is preferably not less than 1.0 mm and more preferably not less than 1.2 mm. As a material of the outer tubular body 12 and the inner tubular body 13, flexible materials having excellent antithrombogenicity are preferred, and examples thereof include fluororesins, polyamide resins, polyurethane resins, polyimide resins, and the like.

As a method for fixing the balloon 9 to each of the outer tubular body 12 and the inner tubular body 13, welding is preferred. Alternatively, the ends of the balloon 9 may be fixed to only either of the outer tubular body 12 or the inner tubular body 13.

The high-frequency current distributing electrode 10 is fixed to the inner tubular body 13, and examples of the fixation method include caulking, adhesives, welding, and heat-shrinkable tubing.

The shape of the high-frequency current distributing electrode 10 is preferably a coil shape. The diameter of an electric wire that forms the coil-shaped high-frequency current distributing electrode 10 and a high-frequency power supply lead is preferably 0.1 to 1 mm and more preferably 0.2 to 0.5 mm. As a material thereof, a highly conductive metal is preferred, and examples thereof include copper, silver, gold, platinum, tungsten, and alloy. Further, to prevent a short circuit, the portions other than coil-shaped portions of the electric wire and the high-frequency power supply lead is more preferably coated with an electrically insulating protective covering such as a fluororesin.

The high-frequency power supply lead is connected to the high-frequency power generator 15 via a high-frequency power generator connector 14 to distribute high-frequency current to the high-frequency current distributing electrode 10.

Examples of the temperature sensor 11 fixed to the inner tubular body 13 include a thermocouple and a resistance thermometer.

A temperature sensor lead connected to the temperature sensor 11 is connected to the high-frequency power generator 15 via the high-frequency power generator connector 14 to transfer temperature signals measured with the temperature sensor 11 to the high-frequency power generator 15.

The diameter of the temperature sensor lead is preferably 0.05 to 0.5 mm. As a material of the temperature sensor lead, when the temperature sensor 11 is a thermocouple, the same material as that of the thermocouple is preferred, and example thereof in the case of a T-type thermocouple include copper and constantan. On the other hand, when the temperature sensor 11 is a resistance thermometer, a highly conductive metal such as copper, silver, gold, platinum, tungsten, or alloy is preferred. Further, to prevent a short circuit, it is more preferable to be coated with an electrically insulating protective covering such as a fluororesin.

As described above, the high-frequency power generator 15 is connected to the high-frequency current distributing electrode 10 through the high-frequency power supply lead and to the temperature sensor 11 through the temperature sensor lead and the high-frequency power generator connector 14, and further connected to a return electrode 18 through a return electrode lead 19.

The balloon is heated by distribution of high-frequency current between the high-frequency current distributing electrode 10 and the return electrode 18 attached to a patient's body surface with the high-frequency power generator 15.

The catheter for measuring electric potential is inserted through a lumen of the inner tubular body 13 of the balloon-tip ablation catheter 8.

EXAMPLES

Specific examples of the catheter for measuring electric potential will now be described referring to the Drawings. It should be understood that "length" as used herein represents the length in the longitudinal direction.

Example 1

A medical tubing apparatus was used to prepare a polyurethane tube with an outer diameter of 1.2 mm, an inner diameter of 0.9 mm, and a length of 1200 mm. Starting from the position 50 mm from the distal end of the polyurethane tube, eight holes with a diameter of 1 mm for the passage of electric potential-measuring electrode leads were made at 5-mm intervals to produce a shaft 3 of a catheter for measuring electric potential.

Using a silver-plated copper pipe with an outer diameter of 1.2 mm and a length of 1 mm as an electric potential-measuring electrode 2 and copper wires with a diameter of 0.1 mm as electric potential-measuring electrode leads 7, the electric potential-measuring electrodes 2 and the electric potential-measuring electrode leads 7 were joined with solder. The electric potential-measuring electrode leads 7 were coated with an electrically insulating protective covering of fluororesin. Eight parts connecting the electric potential-measuring electrodes 2 to the electric potential-measuring electrode leads 7 were produced.

The electric potential-measuring electrode leads 7 of the parts described above were each inserted into eight holes in the shaft 3, and the electric potential-measuring electrodes 2 and the holes were fixed by caulking.

In the region where eight electric potential-measuring electrodes 2 are attached in a row, shape-memory alloy wires with a diameter of 1 mm and a length of 80 mm were fixed inside the lumen of the shaft 3 to form the region described above into a loop shape.

Using a stainless wire with an outer diameter of 1.2 mm and a length of 10 mm as a distal metal portion 5, a metal wire 6 with an outer diameter of 0.4 mm and a length of 900 mm was connected thereto by soldering.

The metal wire 6 was inserted from the distal side of the shaft 3, and the proximal end of the distal metal portion 5 and the distal end of the shaft 3 were joined by fixation with an adhesive. The metal wire 6 inserted into the shaft 3 was not connected to the electric potential-measuring apparatus connector 4 to be electrically insulated at the proximal side in the shaft 3.

Each of the electric potential-measuring electrode leads 7 was taken out from the proximal end of the shaft 3, and all of them were connected to the electric potential-measuring apparatus connector 4, after which the proximal end of the shaft 3 and the electric potential-measuring apparatus connector 4 were fixed with an adhesive and a heat-shrinkable tube to prepare a catheter for measuring electric potential (hereinafter referred to as "the catheter for measuring electric potential of Example 1").

Example 2

A catheter for measuring electric potential was prepared in the same manner as in Example 1 except using a stainless wire with an outer diameter of 1.2 mm and a length of 9 mm as the distal metal portion 5 (hereinafter referred to as "the catheter for measuring electric potential of Example 2").

Example 3

A catheter for measuring electric potential was prepared in the same manner as in Example 1 except using a stainless wire with an outer diameter of 1.2 mm and a length of 8 mm as the distal metal portion 5 (hereinafter referred to as "the catheter for measuring electric potential of Example 3").

Example 4

A catheter for measuring electric potential was prepared in the same manner as in Example 1 except using a stainless wire with an outer diameter of 1.2 mm and a length of 7 mm as the distal metal portion 5 (hereinafter referred to as "the catheter for measuring electric potential of Example 4").

Example 5

A catheter for measuring electric potential was prepared in the same manner as in Example 1 except using a stainless wire with an outer diameter of 1.2 mm and a length of 6 mm as the distal metal portion 5 (hereinafter referred to as "the catheter for measuring electric potential of Example 5").

Example 6

A catheter for measuring electric potential was prepared in the same manner as in Example 1 except using a stainless wire with an outer diameter of 1.2 mm and a length of 5 mm as the distal metal portion 5 (hereinafter referred to as "the catheter for measuring electric potential of Example 6").

Example 7

A catheter for measuring electric potential was prepared in the same manner as in Example 1 except using a stainless wire with an outer diameter of 1.2 mm and a length of 4 mm as the distal metal portion 5 (hereinafter referred to as "the catheter for measuring electric potential of Example 7").

Example 8

A catheter for measuring electric potential was prepared in the same manner as in Example 1 except using a stainless wire with an outer diameter of 1.2 mm and a length of 3 mm as the distal metal portion 5 (hereinafter referred to as "the catheter for measuring electric potential of Example 8").

Example 9

A catheter for measuring electric potential was prepared in the same manner as in Example 1 except using a stainless wire with an outer diameter of 1.2 mm and a length of 2 mm as the distal metal portion 5 (hereinafter referred to as "the catheter for measuring electric potential of Example 9").

Comparative Example 1

A catheter for measuring electric potential was prepared in the same manner as in Example 1 except using a stainless wire with an outer diameter of 1.2 mm and a length of 1 mm as the distal metal portion 5 (hereinafter referred to as "the catheter for measuring electric potential of Comparative Example 1").

Comparative Example 2

A catheter for measuring electric potential was prepared in the same manner as in Example 1 except that the distal metal portion 5 and the metal wire 6 were not attached (hereinafter referred to as "the catheter for measuring electric potential of Comparative Example 2"). Preparation of balloon-tip ablation catheter A balloon-tip ablation catheter 8 through the lumen of which the catheter for measuring electric potential is inserted was prepared by the following procedure.

First, a glass balloon mold having a mold surface corresponding to a desired balloon shape was immersed in a polyurethane solution at a concentration of 13% by weight, and a polyurethane balloon 9 with a diameter of 30 mm and a thickness of 120 μm was prepared by the dipping method in which a solvent (dimethylacetamide) is evaporated by heating at 70° C. to form a urethane polymer coating on the mold surface.

An outer tubular body 12, which was a polyurethane tube with an outer diameter of 4 mm, an inner diameter of 3 mm, and a total length of 1000 mm, was provided at its proximal end with a luer lock 16, and insertion-fitted and adhesively fixed to a Y-shaped connector 17.

Starting from the position 20 mm from the distal end of an inner tubular body 13, which is a polyurethane tube with an outer diameter of 1.8 mm, an inner diameter of 1.4 mm, and a total length of 1100 mm, a high-frequency power supply lead with a diameter of 0.5 mm the electrically insulating protective covering of which was partially peeled off was directly wound around the inner tubular body 13 to form a 10-mm-long coil shape, which was used as a high-frequency current distributing electrode 10.

Using an ultrathin thermocouple copper wire coated with an electrically insulating protective covering as one temperature sensor lead and an ultrathin thermocouple constantan wire coated with an electrically insulating protective covering as the other temperature sensor lead, the tips of the temperature sensor leads were joined with solder, and the joining point was defined as a temperature sensor 11. The temperature sensor 11 was arranged at the position 1 mm from the proximal end of the high-frequency current distributing electrode 10.

The inner tubular body 13 to which the high-frequency current distributing electrode 10 and the temperature sensor 11 were fixed was inserted from the proximal side of the Y-shaped connector 17 into the outer tubular body 12, and the inner tubular body 13 and the outer tubular body 12 were fixed at the proximal side.

The high-frequency current distributing lead and the temperature sensor lead were connected to the high-frequency power generator connector 14 through the space between the outer tubular body 12 and the inner tubular body 13 and through the Y-shaped connector 17, and further the Y-shaped connector 17 was connected to the high-frequency power generator connector 14.

Finally, the distal end of the balloon 9 was heat-welded to the outer periphery 10 mm from the distal end of the inner tubular body 13, and the proximal end of the balloon 9 was heat-welded to the outer periphery near the distal end of the outer tubular body 12, respectively, thereby completing the balloon-tip ablation catheter 8.

Construction of Balloon-Rip Ablation Catheter System

The catheters for measuring electric potential of Examples 1 to 9 and Comparative Examples 1 and 2 prepared were each inserted from the proximal end of the inner tubular body 13 of the balloon-tip ablation catheter 8 through its lumen, and the electric potential-measuring electrodes 2 was exposed near the distal end of the balloon 9 to construct a balloon-tip ablation catheter system for each catheter for measuring electric potential.

Figure 4:
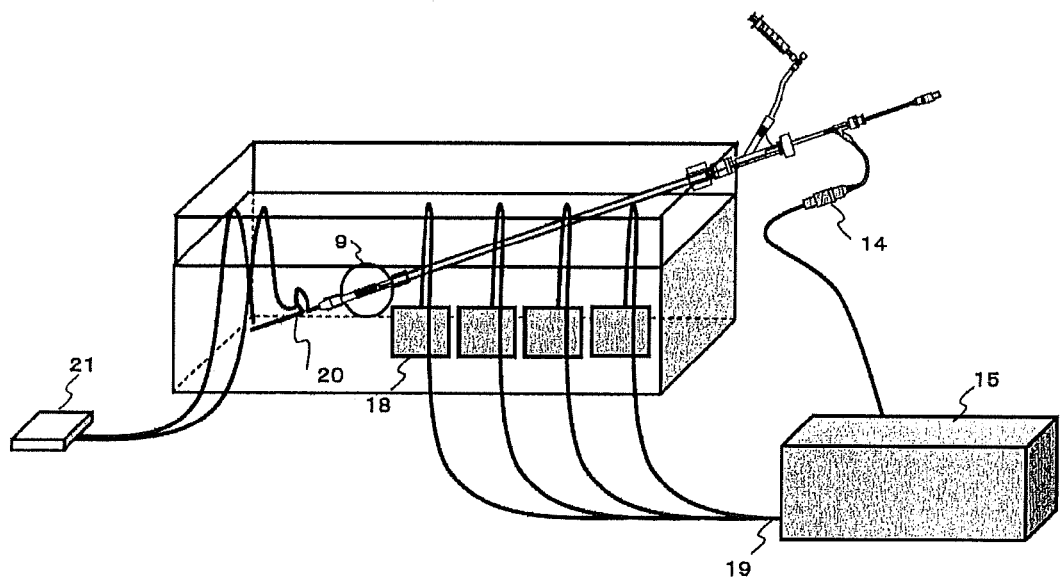
FIG. 4 illustrates a test system for measuring the temperature of electric potential-measuring electrodes and a distal metal portion.

Temperature Measurement of Electric Potential-Measuring Electrodes and Metal Portion FIG. 4 illustrates a test system for measuring the temperature of electric potential-measuring electrodes and a distal metal portion.

The balloon 9 of the balloon-tip ablation catheter system was inflated with physiological saline such that the greatest dimension was 30 mm and immersed in a water tank filled with physiological saline. Further, the return electrode 18 for distributing high-frequency current was immersed in the same water tank, and then the high-frequency power generator connector 14 and the return electrode lead 19 were connected to the high-frequency power generator.

High-frequency current (frequency: 1.8 MHz, maximum electric power: 150 W, preset temperature: 70° C.) was distributed between the return electrode and the high-frequency current distributing electrode to heat the balloon, and an electric potential-measuring electrode temperature and a distal metal portion temperature were each measured with a T-type thermocouple 20 connected to a temperature data logger 21. The temperature measurements were continued for 5 minutes from the start of the distribution of high-frequency current, and the maximum temperature of each was taken as the electric potential-measuring electrode temperature and the distal metal portion temperature.

Temperature Measurement Results of Electric Potential-Measuring electrodes and Distal Metal Portion Table 1 shows the measurement results of the electric potential-measuring electrode temperature and the distal metal portion temperature of each balloon-tip ablation catheter system through which the catheter for measuring electric potential of Examples 1 to 9 or Comparative Example 1 or 2 was inserted.

TABLE 1

| Catheter for measuring electric potential | Distal Metal Portion Length [mm] | Electric Potential-Measuring Electrode Temperature [° C.] | Distal Metal Portion Temperature [° C.] |
| --- | --- | --- | --- |
| Example 1 | 10 | 38.5 | 41.5 |
| Example 2 | 9 | 38.2 | 43.5 |
| Example 3 | 8 | 38.5 | 43.9 |
| Example 4 | 7 | 38.0 | 44.1 |
| Example 5 | 6 | 38.9 | 43.4 |
| Example 6 | 5 | 39.8 | 44.9 |
| Example 7 | 4 | 40.3 | 50.1 |
| Example 8 | 3 | 40.1 | 51.4 |
| Example 9 | 2 | 42.8 | 54.9 |
| Comparative Example 1 | — | 65.7 | — |
| Comparative Example 2 | 1 | 48.5 | 76.7 |

The catheter for measuring electric potential of Comparative Example 2 which does not have a distal metal portion had an electric potential-measuring electrode temperature of 65.7° C., exceeding 65° C. which is a temperature causing pulmonary vein stenosis.

On the other hand, although the catheters for measuring electric potential of Examples 1 to 9 and Comparative Example 1 which have a distal metal portion caused no abnormal heat generation exceeding 65° C. at electric potential-measuring electrodes, the catheter for measuring electric potential of Comparative Example 1 caused abnormal heat generation (76.7° C.) at a distal metal portion.

From the results in Table 1, it is apparent that the catheters for measuring electric potential of Examples 1 to 9 which have a distal metal portion length of 2 mm or more did not cause an abnormal heat generation at electric potential-measuring electrodes or at a distal metal portion, and that, in particular, the catheters for measuring electric potential of Examples 1 to 6 which have a distal metal portion length of 5 mm or more can reduce the heat generation at electric potential-measuring electrodes and a distal metal portion to 50° C. or lower. These results are presumably because the high-frequency current density on a distal metal portion surface can be reduced to a low level by ensuring the distal metal portion length of 2 mm.

INDUSTRIAL APPLICABILITY

Our catheters can be used in the medical field to measure electric potential that can be used in combination with a balloon-tip ablation catheter.

The invention claimed is:

1. A catheter that measures electric potential comprising:
a shaft having electric potential-measuring electrodes, a metal portion with a length of 2 mm or more, and a lumen passing therethrough from a proximal end to a distal end in a longitudinal direction; and
a metal wire inserted through said lumen and connected to said metal portion, wherein a proximal end of the metal wire does not have any electrical connection.

2. The catheter according to claim 1,
wherein said electric potential-measuring electrodes are attached at a distal side in the longitudinal direction of said shaft, and
said metal portion is located distally relative to a position of said electric potential-measuring electrodes in the longitudinal direction of said shaft.

3. The catheter according to claim 2, wherein said metal portion has a length of 2 to 50 mm.

4. The catheter according to claim 1, wherein said metal portion has a length of 2 to 50 mm.

5. The catheter according to claim 1, wherein said metal wire is electrically insulated.

6. A balloon-tip ablation catheter system comprising:
the catheter according to claim 1; and
a balloon-tip ablation catheter comprising a lumen passing therethrough from a proximal end to a distal end in the longitudinal direction,
wherein said catheter for measuring electric potential is inserted through the lumen of said balloon-tip ablation catheter.

* * * * *